United States Patent
Bhonde et al.

(10) Patent No.: US 6,790,659 B2
(45) Date of Patent: Sep. 14, 2004

(54) IN VITRO PRODUCTION OF AMOEBOCYTES FROM TACHYPLEUS GIGAS IN LEIBOVITZ CULTURE MEDIUM

(75) Inventors: Ramesh Ramchandra Bhonde, Pune (IN); Anil Chatterji, Gora (IN)

(73) Assignees: Council of Scientific and Industrial Research, New Delhi (IN); National Center for Cell Sciences, Pune (IN)

(*) Notice: Subject to any disclaimer, the term of this patent is extended or adjusted under 35 U.S.C. 154(b) by 91 days.

(21) Appl. No.: 10/109,543

(22) Filed: Mar. 28, 2002

(65) Prior Publication Data

US 2003/0186432 A1 Oct. 2, 2003

(51) Int. Cl.[7] .............................. C12N 5/00; C12N 5/02
(52) U.S. Cl. ...................... 435/325; 435/395; 435/404; 435/408
(58) Field of Search .................. 435/325, 395, 435/404, 408

(56) References Cited

U.S. PATENT DOCUMENTS 5,082,782 A * 1/1992 Gibson et al. .............. 435/378

* cited by examiner

Primary Examiner—David M. Naff
Assistant Examiner—Deborah K. Ware
(74) Attorney, Agent, or Firm—Ladas & Parry

(57) ABSTRACT

The present invention provides a process for large scale in vitro production of amoebocytes of Indian Horseshoe Crab (*Tachypleus gigas*) (*T. gigas*) from dissected gill flaps of *T. gigas*, in Leibovitz L-15 culture medium concentration (2×), to provide enhanced generation of amoebocytes. The process comprises the steps of: dissecting gill flaps of *T. gigas*; washing the gill flaps with an antibiotic solution followed by alcohol; culturing the gill flaps in tissue culture plates of sterile saline on a Rocker platform; culturing further the gill flaps in Leibovitz L-15 culture medium (2×); purging the gill flaps with Tween 80 solution; and purging again the gill flaps with horseshoe crab serum, while keeping the gill flaps in the culture medium viable for 90 days by feeding with fresh medium at an interval of 10–15 days to enable the enhanced release of amoebocytes both within and outside the gill flaps.

10 Claims, No Drawings

IN VITRO PRODUCTION OF AMOEBOCYTES FROM TACHYPLEUS GIGAS IN LEIBOVITZ CULTURE MEDIUM

FIELD OF INVENTION

The present invention relates process for the in vitro culture for the production of Indian horseshoe crab (*Tachypleus gigas*) amoebocytes.

BACKGROUND AND PRIOR ART REFERENCES

The blood or haemolymph of the horseshoe crab is an important source for the preparation of a diagnostic reagent—the amoebocyte lysate useful in the detection gram-negative bacteria.

The preparation of amoebocyte lysate where the haemolymph is directly collected from the wild Indian horseshoe crab, though the technology is viable, as the technology requires regular supply of the blood from the live horseshoe cabs which may lead to indiscriminate killing.

The process of production of amoebocyte in vitro from the American horseshoe crab (*Limulus polyphemus*) was also patented (U.S. Pat. No. 5,082,782).

Reference may be made to a publication wherein amoebocytes were cultured in liquid media from open surface of the gill lamellae of *Limulus polyphemus*. The drawback of the process was short termed culture (seven days only of the amoebocytes (Hilly J. B; Gibson III D. G.,1989. Culture of amoebocytes on opened gill lamellae of the horseshoe crab, *Limulus polphemus*. *American Zoologist*, 29 (4) 112 A.

Reference may be made to another publication wherein culture of amoebocyte was carried out in a nutrient mist bioreactor with little growth amoebocyte restricted to only seven day. The drawback of this process was fungal contamination (Friberg J. A; Weathers P. J; Gibson III D. G., 1992. Culture of amoebocytes in a nutrient mist bioreator. In vitro 28 A3 pp 215–217.

Reference may be made to a publication wherein gill flaps removed from American horseshoe crabs were cultured using Grace's Insect medium at pH 7.6, maintaining the culture on a shaker table for 5–12 days at 23–37° C. and obtaining the amoebocytes by pulsing with a solution of 10–20% Limulus serum (Daniel G. Gibson, III, Teaticket, Joan B., Hilly, Uxbridge, 1992, U.S. Pat. No. 5,082,782. The drawback of the present invention is that the Grace's Insect medium retains the culture viable only for 5–12 days.

Reference may be made to our earlier patents where the amoebocytes were separated from the haemolymph directly collected from the wild horseshoe crab. The drawbacks of the invention were primarily fluctuating trend in the availability of the horseshoe crab for the collection of haemolymph, seasonal variations in the sensitivity of lysate and threat for depletion of this valuable animals due to over exploitation (Chatterji, A. 1997, An improved process for the preparation of *Tachypleus Amoebocyte* Lysate (TAL) useful for detection of pyrogens in vitro, NF-235/97).

Accordingly, the present invention provides a new medium for the production of Indian horseshoe crab (*Tachypleus gigas*) amoebocytes in vitro to one reported earlier wherein Grace's Insect Medium was used to cultivate the gill flaps. In the new medium, the Grace's Insect medium was replaced by sterilized normal saline with 720 mOsm, followed by culturing in (2×) L-15 medium Leibovitz medium (L-15) 2× concentration.

OBJECTS OF THE INVENTION

The main object of the present investigation is to provide a process for the production of Indian horseshoe crab (*Tachypleus gigas*) amoebocytes in vitro.

Another object of the present invention is to provide a new medium to keep amoebocytes viable for 90 days without any morphological change.

Yet another object of the present invention is to obtain large-scale production of amoebocyte in vitro from horseshoe crab.

Still another object of the present invention is to prepare high quality amoebocyte lysate without seasonal variability.

Yet another object of the present invention is to avoid batch to batch variability in the sensitivity of amoebocyte lysate.

Still another object of the present invention is to continuously produce amoebocyte in vitro reducing the cost of production of amoebocyte lysate.

SUMMARY OF THE INVENTION

The present invention comprises dissecting gill flaps from the Indian horseshoe crab (*T. gigas*), washing the organ at first with an antibiotic (5% betadine) solution for 10 minutes, further washing the organ with 70% alcohol for 10 minutes, culturing the organ in 6 well tissue culture plates containing sterilized normal saline 720 mOsm on a Rocker platform at 23–28° C. for 48 hours, followed by culturing in 2×L-15 for another 48 hours. Gill flaps were purged with 1% Tween 80 solution followed by further purging with 10% horseshoe crab serum (haemolymph without amoebocyte), leading to release of amoebocyte within and outside the gill flaps. The cultures were fed at an interval of 5–10 days with fresh medium. In this present invention, the culture of amoebocyte was maintained for 90 days and there was no change observed in their morphology and viability.

DETAILED DESCRIPTION OF THE INVENTION

Accordingly, the present invention provides a process for large scale in vitro production of amoebocytes of Indian Horseshoe Crab (*Tachypleus gigas*) from dissected gill flaps of *T. gigas*, in Leibovitz culture medium concentration (2×L-15), having enhanced generation of amoebocytes, said process comprising the steps of:

(a) dissecting gill flaps of *T. gigas*;

(b) washing the gill flaps initially with an antibiotic solution for 10 minutes followed by alcohol;

(c) culturing the gill flaps in tissue culture plates of sterile saline on a Rocker platform at a temperature ranging between 23–28° C.;

(d) culturing further the gill flaps of step (c) in Leibovitz culture medium (2×L-15);

(e) purging the gill flaps with Tween 80 solution; and (f) purging again the gill flaps with horse crab serum, keeping the culture viable for 90 days by feeding with fresh medium at an interval of 10–15 days to enable the enhanced release of amoebocytes both within and outside the gill flaps.

In an embodiment of the invention provides a process, wherein in step (a) the gill flaps from the Indian horseshoe crab (*T. gigas*) are removed and dissected under highly aseptic condition.

Still another embodiment of the invention, the preferable antibiotic for washing of gill flaps in step (b) is selected from betadine 5–10% solution.

Still another embodiment of the invention, alcohol used for further washing in step (b) is having a concentration ranging between (70–90%) for about 10–15 minutes. Still another embodiment, the gill flaps in step (c), are cultured in 6-well tissue culture plates containing sterilized normal saline 720 mOsm on a Rocker platform for a period of 48–72 hours.

Yet another embodiment of the invention, further culturing of gill flaps in step (d) are performed in 2×L-15 for a period of 48 hours.

Yet another embodiment, purging of gill flaps in step (e) is done with 1–5% Tween 80 solution.

Yet another embodiment of the invention, further purging in step (f) is performed with 10–15% horseshoe crab serum, leading to enhanced release of amoebocytes within and outside the gill flaps.

Yet another embodiment, the horse crab serum in step (f) is a haemolymph without amoebocytes.

Yet another embodiment of the invention, the culture is in step (f) maintained for 90 days with intermittent feeding of fresh medium.

Yet another embodiment, the said process is performed in pyrogen free atmosphere.

In an embodiment, the gill flaps from the Indian horseshoe crab (*T. gigas*) is removed under highly aseptic condition.

In an embodiment, the gill flaps are washed with an antibiotic (5–8% betadine) solution for 10–15 minutes.

In an embodiment, the gill flaps are further washed with 70–90% alcohol for 10–15 minutes.

In an embodiment, the gill flaps are cultured in 6 well tissue culture plates containing sterilized normal saline 720 mOsm on a Rocker platform at 23–28° C. for 48–72 hours, followed by culturing in 2×L-15 medium.

In an embodiment, the gill flaps are purged with 1–5% Tween 80 solution followed by further purging with 10–15% horseshoe crab serum (haemolymph without amoebocyte), leading to release of amoebocyte within and outside the gill flaps.

In an embodiment, the culture of amoebocyte is maintained for 90 days and the cultures are fed at an interval of 5–10 days with fresh medium.

1) Removal of gill flaps: The gill flaps from the Indian horseshoe crab (*T. gigas*) are removed under highly aseptic condition.
2) Sterilization of gill flaps: The gill flaps are washed with an antibiotic (5% betadine) solution for 10 minutes followed by further washing with 70% alcohol for 10 minutes.
3) Culturing of gill flaps: The gill flaps are cultured in 6 well tissue culture plates containing sterilized normal saline 720 mOsm on a Rocker platform at 23° C. for 48 hours, followed by culturing in (2×) L-15 for another 48 hours. The culture of amoebocyte is maintained for 90 days and the cultures are fed at an interval of 5–10 days with fresh medium.
4) Collection of amoebocytes: The gill flaps are purged with 1% Tween 80 solution followed by further purging with 10–15% horseshoe crab serum (haemolymph without amoebocyte) which lead to release of amoebocyte within and outside the gill flaps.

The aforesaid process requires absolute precaution for pyrogen contamination at all processing steps. All apparatus and reagents must therefore, be pyrogen free.

Main advantage of the present invention:

The novelty and advantage of the present invention is the production of horseshoe crab amoebocyte in vitro from the gill flaps making use of simple salt solution initially followed by 2×L-15 nutrient media thus eliminating the chances of contamination and economizing the process.

Another advantage of the present invention is that the new medium maintains the culture viable for 90 days without any change in the morphology of the amoebocytes.

EXAMPLE-1

Gills of Indian horseshoe crab were maintained in L-15 (2×). After 48 hours of incubation, the gills were purged with Tween 80 and haemolymph. Amoebocytes were seen releasing from the gills and termed as amoebocyte harvest. Count was taken after subsequent harvest. Gills were maintained in vitro for a period of 30 days with six intermittent harvests. After each harvest, gill lamellae were maintained in plain 2×L15 for 48 hours and then again purged with Tween 80 and haemolymph. The culture was maintained for 90 days and fed at an interval of 5–10 days with fresh medium.

What is claimed is:

1. A process for large scale in vitro production of amoebocytes from Indian Horseshoe Crab (*Tachypleus gigas*) (*T. gigas*), said process comprising the steps of:
   (a) dissecting gill flaps of *T. gigas*;
   (b) washing the gill flaps initially with an antibiotic solution for 10 minutes followed by alcohol;
   (c) culturing the gill flaps in tissue culture plates of sterile saline on a Rocker platform at a temperature ranging between 23–28° C.;
   (d) culturing further the gill flaps of step (c) in Leibovitz L-15 culture medium at a concentration of 2×;
   (e) purging the gill flaps in the culture medium with Tween 80 solution; and
   (f) purging again the gill flaps with horseshoe crab serum, while keeping the gill flaps in the medium culture viable for 90 days by feeding with fresh medium at an interval of 10–15 days to enable the enhanced release of amoebocytes both within and outside the gill flaps.

2. A process according to claim 1 wherein in step (a), the gill flaps from the Indian horseshoe crab are removed and dissected under highly aseptic condition.

3. A process according to claim 1 wherein in step (b), the antibiotic for washing of gill flaps is a 5–10% solution of betadine.

4. A process according to claim 1 wherein in step (b), alcohol used for further washing has a concentration ranging between 70–90% for about 10–15 minutes.

5. A process according to claim 1 wherein in step (c), the gill flaps are cultured in 6-well tissue culture plates containing sterilized normal saline 720 mOsm on a Rocker platform for a period of 48–72 hours.

6. A process according to claim 1 wherein in step (d), further culturing of gill flaps is performed in for a period of 48 hours.

7. A process according to claim 1 wherein in step (e), purging of gill flaps is done with 1–5% Tween 80 solution.

8. A process according to claim 1 wherein in step (f), further purging is performed with 10–15% horseshoe crab serum.

9. A process according to claim 1 wherein in step (f), the horseshoe crab serum is a haemolymph without amoebocytes.

10. A process according to claim 1, wherein said process is performed in pyrogen free atmosphere.

* * * * *